Figure 1:
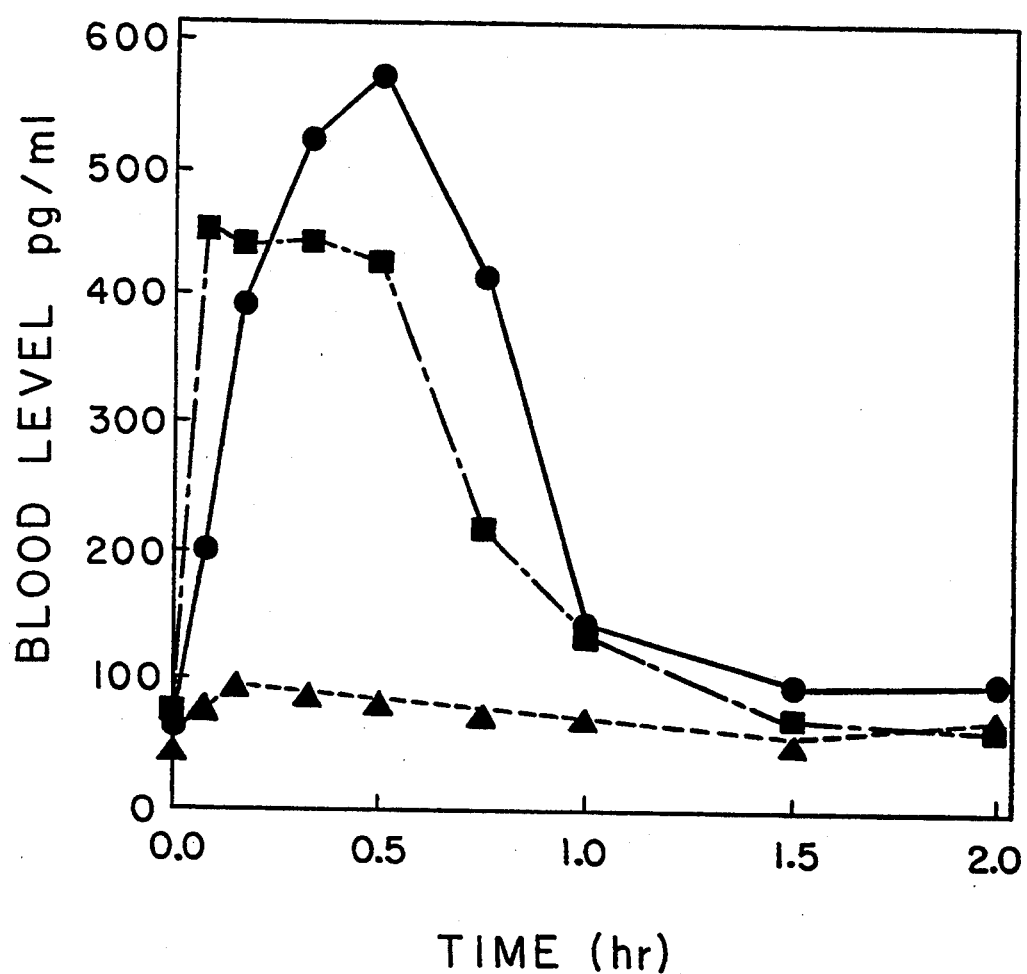

United States Patent [19]
Yamamoto et al.

[11] Patent Number: 5,407,911
[45] Date of Patent: Apr. 18, 1995

[54] PARATHYROID HORMONE-CONTAINING EMULSION FOR NASAL ADMINISTRATION

[75] Inventors: Nakayuki Yamamoto, Tagata; Michihiko Sugimoto, Numazu; Seiki Morimoto, Tagata; Hideo Sakakibara, Shizuoka; Masaru Saita, Miyaki; Yuji Shimozono, Tosu; Takafumi Manako, Miyaki, all of Japan

[73] Assignees: Asahi Kasei Kogyo Kabushiki Kaisha, Osaka; Hisamitsu Keiyaku Kabushiki Kaisha, Saga, both of Japan

[21] Appl. No.: 211,035
[22] PCT Filed: Sep. 16, 1992
[86] PCT No.: PCT/JP92/01179
§ 371 Date: May 16, 1994
§ 102(e) Date: May 16, 1994
[87] PCT Pub. No.: WO93/05805
PCT Pub. Date: Apr. 1, 1993

[30] Foreign Application Priority Data
Sep. 17, 1991 [JP] Japan .................... 3-236193

[51] Int. Cl.$^6$ .................. A61K 37/24; A61K 9/107; A61K 47/26
[52] U.S. Cl. ........................... 514/2; 514/12; 514/947
[58] Field of Search ................ 514/2, 12, 947

[56] References Cited

U.S. PATENT DOCUMENTS

| | | |
|---|---|---|
| 4,695,465 | 9/1987 | Kigasawa et al. ............... 514/947 |
| 4,882,359 | 11/1989 | Nakagawa et al. ............. 514/947 |
| 5,059,587 | 10/1991 | Yamamoto et al. ............. 514/12 |
| 5,238,917 | 8/1993 | Fujii et al. ........................ 514/2 |
| 5,281,580 | 1/1994 | Yamamoto et al. ............. 514/12 |

FOREIGN PATENT DOCUMENTS

| | | |
|---|---|---|
| 62-238261 | 10/1987 | Japan . |
| 1-233230 | 9/1989 | Japan . |
| 2-28121 | 1/1990 | Japan . |
| 4-46129 | 2/1992 | Japan . |

Primary Examiner—Ronald W. Griffin
Attorney, Agent, or Firm—Young & Thompson

[57] ABSTRACT

A parathyroid hormone-containing emulsion for nasal administration, comprising parathyroid hormone as the active ingredient, at least, azacycloalkane derivative of the general formula [1]:

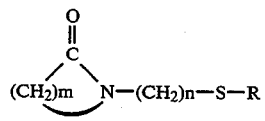

wherein R is alkyl, m is an integer of 2-4, and n is an integer of 1-15, provided that R is alkyl of $C_{5-11}$ in case where n is 1-3, as the absorption promotor, glycyrrhizic acid or its non-toxic salt, and a suitable amount of water.

9 Claims, 1 Drawing Sheet

PARATHYROID HORMONE-CONTAINING EMULSION FOR NASAL ADMINISTRATION

FIELD OF THE INVENTION

The present invention relates to an emulsion for nasal administration containing a parathyroid hormone or its analogue (hereinafter generally designates as PTH) as an active ingredient. More particularly, it relates to such emulsion for nasal administration, having superior stability, and being so improved that the PTH is absorbed safely and efficiently through spraying administration in the nasal cavity.

PRIOR ARTS

Physiologically active peptides are becoming one of the fields where the most progressive development is effected as future therapeutic drugs. However, the present conventional route of administration for the peptide drugs are almost limited to injection. Thus, a more simple administrating preparation which can be adminsitered by self-medication has been desired, especially in the treatments of the chronic disorders, to avoid the inconvenient of going to hospital regularly, and for the purpose of diminishing pain and anguish at the site of injection.

Recently, there have been many attempts to develop alternative administration, e.g. rectal, nasal, oral, etc., instead of injection route. It has been found that absorption of peptides, which are poorly absorbed through mucosain the form of a normal drug preparation, can be enhanced by addition of surface active agents, and accordingly several absorption promoters have been found. For example, among the report on nasal administration of physiologically active peptides, nasal adminsitration of aqueous insulin preparation using sodium glycodeoxycholate as an absorption promoter has been known. [Proc. Natl. Acad. Sci. U.S.A., 82 (21), 7419-7423 (1985)]. Further nasal administration of polypeptide using biel acid such as cholic acid, deoxycholic acid and taurocholic acid, has known (Japanese Patent Unexamined Publication, No. 63-2932). A powdery nasal administration preparation consisting of physiologically active peptides and aqueous absorbable and water-less-soluble base ingredients has also known. (Japanese Patent Unexamined Publication, No. 60-224616) However, these preparations are not satisfactory due to the inferior absorbability and local irritation and are not yet practically employed.

Among various physiologically active peptides, parathyroid homons are generally known as a peptide hormone having serum calcium elevating activity, and are used clinically as diagnostic agent for hypoparathyroidism. But, it has been known that PTH are a highly hydrophillic peptide with a higher molecular weight (approximately 4,000-10,000) and much poorly absorbed through the gastrointestinal tract.

PROBLEMS TO BE SOLVED BY THE INVENTION

Azacycloalkane derivatives was disclosed to exhibit superior absorption promoting effect. (Japanese Patent Unexamined Publication, No. 62-238261) It was found that these derivativs have much stronger absorption promoting effect with physiological properties different from those absorption promotors used in the conventional preparations for nasal administration. Accordingly, PTH preparations for nasal administration were prepared using such derivatives as the absorption promotor, however, satisfactory results were not obtained since the emulsifying agent required for emulsification, heretofore used, were insufficiently effected.

Also many studies have been conducted recently on emulsions which are a liquid preparation containing water and oil in homogeneous state. Many emulsifying agents have been developed, and much stable emulsions have been broadly used, owing to the significant progress in emulsifying techniques.

However, the majority of the emulsions are those using a nonionic surface active agent having a polyoxyethylene chain, or an ionic surface active agent, as the emulsifying agent, many of which are, in turn, had a strong suspicion about the safety to human body. Further, egg-york lecithin and soybean lecithin may be referred to as the emulsifying agent commonly used for fatty emulsions for intravenous injection. These emulsions have, however, certain problems in their insufficient stability at room temperatures, as well as their homogeneity.

The present invention has been accomplished in order to deal with such problems.

An object of the present invention is to provide a PTH emulsion preparation for nasal administration having excellent stability, when using azacyclo-alkane derivative as the absorption promotor.

MEANS FOR SOLVING THE PROBLEMS

In the course of studies on emulsifying agents suitable to such emulsion preparations, the present inventors have found that glycyrrhizic acid or its non-toxic salt, which has been thought to have a weak solubilizing activity, has stronger solubilizing power than that of, as compared with, nonionic surface active agents such as HCO-60 [polyoxyethylene(60) hydrogeneated castor oil, NIKKO CHEMICALS CO.] and polysorbate 80 [generic name, polyoxyethylene (20) sorbitran monooleate, NIKKO CHEMICALS CO.], and is unexpectedly well suited for the emulsification of PTH nasal administration preparations using an azacycloalkane derivative as the absorption promotor, thus yielding a stable emulsion with homogeneous fine particles.

Therefore, the present invention relates to a PTH-containing emulsion for nasal administration, which is characterized by having a PTH as the active ingredient, and containing, at least, an azacycloalkane derivative of the general formula [1]:

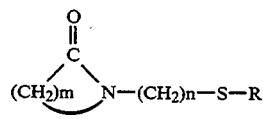

[1]

wherein R is alkyl, m is an integer of 2-4, and n is an integer of 1-15, provided that R is alkyl of $C_{5-11}$ in case where n is 1-3, as the absorption promotor, glycyrrhizic acid or its non-toxic salt, and a suitable amount of water.

PTH as the active ingredient in the present invention is commonly known as peptide hormones of molecular weight of approximately 4,000-10,000 having serum calciuim increasing activity (serum hypercalcemic activity) with 34-84 amino acid sequence and natural type parathyroid hormone or its analogues has been known. Examples thererof are human-PTH(1-84)[h-PTH(1-84)] [Biochemistry, 17, 5723 (1978)], h-

PTH(1-38) (Japanese Patent Unexamined Publication, No. 57-81448), h-PTH(1-34) [Hoppe seyler's Z. Physiol. Chem., 355, 415 (1974)], h-PTH (1-34)NH$_2$ (Japanese Patent Unexamined Publication, No. 58-96052), [Nle 8, 18]h-PTH(1-34), [Nle 8, 18, Tyr 34]h-PTH(1-34) (Japanese Patent Unexam. Publ., No. 55-113753), [Nle 8, 18]h-PTH(1-34)NH$_2$ (Japanese Patent Unexam. Publ., No. 61-24598), [Nle 8, 18, Tyr 34]h-PTH(1-34)NH$_2$ (Japanese Patent Unexam. Publ., No. 60-34996), Rat-PTH(1-84) [J. Biol. Chem., 259 (5), 3320 (1984)], Rat-PTH-(1-34) [Endocrinol., 117 (3), 1230 (1985)], Bovine-PTH(1-84) [Am. J. Med., 50, 639 (1971)], Bovine-PTH(1-34), Bovine-PTH (1-34)NH$_2$ [Pathobiology Annual, 11, 53 (1981)]. Preferable example is h-PTH(1-34) having molecular weight approximately 4,400 with 34 amino acid sequence. In this invention the natural type parathyroid hormone or its analogues illustrated hereinabove is simply defined as parathyroid hormon or abbrebiated as PTH, namely parathyroid hormone in the present invention, which includes parathyroid hormone analogues and abbrebiated as PTH, includes the above illustrated examples.

In the present invention, ordinary PTH concentration in the PTH emulsion for nasal administration is 10-10,000 Units, more preferably, 100-1,000 Units, per milliliter of the preparation.

The azacycloalkane derivatives used as the absorption promotor in the present invention are an oily material, which are included in the above general formula [1] hereinbefore and illustrated in the Japanese Patent Unexamined Publication, No. 62-238261. Embodiments of the R in the general formula [1] are straight chain or branched alkyl, such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicocyl and the like. Among them, the preferred absorption promotor is 1-[2-(decylthio)ethyl] azacyclo-pentane-2-one (oil), for which in the formula [1], R being alkyl with $C_{10}$, m is 3 and n is 2.

The amount of such azacycloalkane derivative to be added in the present invention is preferably so as to give a concentration of 0.01%-10% (W/V), more preferably, 0.1%-5% (W/V).

Glycyrrhizic acid and its non-toxic salts, used in the present invention, are known as a natural constituent extracted from licorice (glycyrrhiza) (*Glycyrrhiza glabra* or *Glycyrrhiza radix*), and widely used for cosmetics and food additives such as sweetening agents.

As the glycyrrhizic acid and its non-toxic salts, there may be illustrated glycyrrhizic acid, and dipottasium glycyrrhizate, monoammonium glycyrrhizate, disodium glycyrrhizate, trisodium glycyrrhizate, and the like. The amount to be added of such acid or its salt may be so as to give a concentration of not less than 0.1% (W/V), generally 0.1%-5% (W/V), more preferably 0.5%-2% (W/V), in the preparation.

An amount of water in the present invention means a residual quantity of water when an effective composition of PTH, an absorption promotor of azacycloalkane derivative and an emulsifier of glycyrrhizic acid or its non-toxic salt are set to prepare at the aforesaid concentration, and an amount of water is, for example, 99-85% (W/V) in the preparation.

In general, preparation of nasal administration are conventionally an aqueous liquid formulation either in spray or in drop form. The emulsions of the present invention may be prepared by using, at least, the above-mentioned oily azacycloalkane derivative, glycyrrhizic acid or its non-toxic salt, and a suitable amount of water to give concentrations of the above constituents as mentioned above. An emulsion in the present invention means, in macroscopically, milky white or colorless transparent (colorless clear) homogeneous liquid preparation, which being constituted, in microscopically, W/O emulsion obtained from oily azacycloalkane derivative and a large amount of water. The emulsion can be stabilized by adding glycyrrhizic acid or its non-toxic salt. They are preferably adjusted to a pH of 5-7 and an osmotic pressure ratio against physiological salt solution of about 1. To adjust or maintain pH 5-7, a pH adjusting agent such as sodium hydoroxide, potassium hydroxide, sodium carbonate, sodium hydrogencarbonate, hydrochloric acid, sulfuric acid, or a buffer solution such as acetate, lactate, citrate and phosphate buffer solutions, may be added. To adjust the osmotic pressure ratio to approximately 1, an isotonic agent, preferably glycerol, may be used. If required, sodium chloride, potassium chloride, mannitol, glucose, and the like, may be added.

The composition for nasal administration of the present invention may also contain a appropriate preserving agent as conventional pharmaceutically acceptable excipient. For example, p-oxybenzoate esters, chlorobutanol, phenyl-ethyl alcohol, benzalkonium chloride, phenol, thimerosal, dehydroacetic acid, sorbic acid, and the like, are illustrated. Suitable concentration of such preserving agent is, generally, 0.02%-2% (W/V), varying depending on the preservatives selected.

Emulsions for nasal administration can be prepared by mixing each ingredients in an arbitrary sequence and emulsifying the mixture, according to the well-known procedures. To prepare the emulsions of the present invention, for example, dipotassium glycyrrhizate, h-PTH (1-34), and other additives to be used in the present invention, are added with a suitable amount of distilled water for injection, and the mixture is made to a solution by heating and agitation. Then the solution is adjusted to a desired pH by addition of pH adjustor, for example, sodium hydroxide or hydrochloric acid. After addition of an azacycloalkane derivative as the absorption promotor, the mixture may be allowed to emulsify by the conventional method using an emulsifier. For example, use of Biomixer (NIHON SEIKI SEISAKU-SHO) with 10,000-20,000 rpm agitaiton for 10 min. yields a homogeneously dispersed emulsion, for example, with 0.1-0.3 μm fine particle size. Also, ultrasonic emulsifier and colloid mill, among others, may be used for the preparation. Alternatively, h-PTH (1-34) may be added after the preparation of the emulsion and allowed to dissolve in it. The resulting homogeneous h-PTH (1-34) containing emulsion preparation may be filtered in aseptic condition, for example, through a 0.22 μm membrane filter, and filled, for example, in vials and if required lyophylized to give the final product.

The dosage of the emulsion of the present invention varys depending on the object for the administration, however in case of human, the administration is secured by spraying the emulsion to a naris or nares using a metered-dose spray (0.05-0.1 ml/stroke) each one or twice time of spray stroke with 1-3 times a day.

One object of the PTH emulsion for nasal administration of the present invention is to administer the emulsion in the nasal cavity in the state of mistusing conventional spraying apparatus, thereby to secure the systemic effect. Using the preparation of the present invention, it is possible to make PTH to distribute in the whole body through adhesion of the emulsion in the wide area of the nasal mucosa and substantial permeation through the mucosa. Accordingly, the PTH-containing emulsion for nasal administration of the present invention can be administered to patients having disorders needing the treatment with PTH, even by themselves, without problems such as pain and anguish when administered by injection.

BREIF EXPLANATION OF DRAWINGS

FIG. 1 shows a time-couse variation of h-PTH(1-34) plasma levels after nasal administration of the preparation of the present invention, and the control preparation, and after intramuscular administration of the latter to rats.

Following referential experiments and examples illustrate the present invention but are not construed as limiting the invention.

Referential Experiment 1

Stabilities of Emulsions (1) Experimental method

Using 1-[2-(decylthio)ethyl]azacyclopentan-2-one selected from the azacycloalkane derivatives, and three emulsifying agents hereinbelow, emulsifiabilities and stabilities of the emulsions were examined.

① Dipotassium glycyrrhizate (MARUZEN KASEI)
② HCO-60 (NIKKO CHEMICALS CO.)
③ Polysorbate 80 (NIKKO CHEMICALS CO.)

Each 0.1 g of 1-[2-(decylthio)ethyl]azacyclopentan-2-one was placed in a test tube (10 ml), and thereto was added 5.0 ml of an aqueous solution prepared preliminarily by dissolving each of the above three emulsifying agents in a concentration of 0.1–0.5% (W/V), or water containing none of such agent. The mixutre was agitated under 15,000 rpm for 1 minute by Biomixer (NIHON SEIKI SEISAKUSHO) to prepare each emulsion. The state of dispersion just after the preparation and after 3 days standing at room temperature was observed. The turbidity just after the preparation was measured by absorbance at 650 nm, and used as the index of emulsifiability.

(2) Results

The results are shown in Table 1–3. As obvious from the tables, dipotassium glycyrrhizate which is used in the present invention exhibited at least good emulsification at 0.1–5 % and gave full dissolution at 4–5 %. The control which contained no dipotassium glycyrrhizate gave two phase-separation just after the preparation. Further, the stabilities of the emulsions after 3 days at room temperature were observed. Two-phase separation was observed in emulsions prepared using lower concentrations of HCO-60 and polysorbate 80.

While, as for the turbidity as the index of emulsifiability, dipotassium glycyrrhizate showed lower values, that is, stronger emulsifiability, than HCO-60 and polysorbate 80 when compared at the same concentration level. These results show that dipotassium glycyrrhizate is significantly superior in its emulsifiability and stability of the emulsion to HCO-60 and polysorbate 80 which are emulsifying agent widely used now as the additives for pharmaceuticals.

TABLE 1

(Use of dipotassium glycyrrhizate)

| Concentrations (%) | Just after preparation | After 3 days standing | Turbidity* (650 nm) |
|---|---|---|---|
| 5.0 | Colorless clear | Colorless clear | 0.006 |
| 4.0 | Colorless clear | Colorless clear | 0.006 |
| 3.0 | White clear | White clear | 0.346 |
| 2.0 | White clear | White clear | 0.405 |
| 1.0 | White clear | White clear | 0.437 |
| 0.5 | White clear | White clear | 0.459 |
| 0.1 | White emulsified | White emulsified | 1.284 |
| No addition | Separated two phases | Separated two phases | — |

*Turbidity (650 nm)
0–0.1: colorless transparent
0.1–1.0: white transparent (backside visible when looking through)
1.0–: white emulsified (emulsion like commercially available milk)

TABLE 2

(Use of polysorabate)

| Concentrations (%) | Just after preparation | After 3 days standing | Turbidity* (650 nm) |
|---|---|---|---|
| 5.0 | White clear | White clear | 0.172 |
| 4.0 | White clear | White clear | 0.165 |
| 3.0 | White clear | White clear | 0.244 |
| 2.0 | White clear | White clear | 0.803 |
| 1.0 | White emulsified | White emulsion separated | 1.119 |
| 0.5 | White emulsified | White emulsion separated | 2.619 |

*Turbidity (650 nm)
0–0.1: colorless transparent
0.1–1.0: white transparent (backside visible when looking through)
1.0–: white emulsified (emulsion like commercially available milk)

TABLE 3

(Use of HCO-60)

| Concentrations (%) | Just after preparation | After 3 days standing | Turbidity* (650 nm) |
|---|---|---|---|
| 5.0 | White clear | White clear | 0.317 |
| 4.0 | White clear | White clear | 0.425 |
| 3.0 | White clear | White clear | 0.712 |
| 2.0 | White clear | White clear | 0.915 |
| 1.0 | White emulsified | White emulsion partially separated | 1.119 |
| 0.5 | White emulsified | White emulsion partially separated | 2.877 |

*Turbidity (650 nm)
0–0.1: colorless transparent
0.1–1.0: white transparent (backside visible when looking through)
1.0–: white emulsified (emulsion like commercially available milk)

Referential Experiment 2

Stabilities of the Emulsions According to the Added Concentrations of the Azacycloalkane Derivative (1) Experimental method Each 5 ml of a 1% (W/V) solution preliminarily prepared by dissolving dipotassium glycyrrhizate in distilled water was poured in each of eight 10 ml size test tubes, and thereto was added 1-[2-(decylthio)ethyl] azacyclopentane-2-one selected from the azacycloalkane derivatives so as to make a concentration ranging from 0 to 10%. Then the mixture was agitated for 1 minute using Biomixer (NIHON SEIKI SEISAKUSHO) at 15,000 rpm to prepare each emulsion. The state of dispersion just after the preparation, or after 3 days or 7 days standing at room temperature was observed.

(2) Results

The results are shown in Table 4. As obvious from the table, 1-[2-(decylthio)ethyl]azacyclopentane-2-one selected from the azacycloalkane derivatives exhibited at least good emulsification and gave stable emulsion, within a concentration ranging from 0.01% to 10% at the concentration of 1% dipotassium glycyrrhizate in the present invention.

TABLE 4

Stabilities of emulsion relating to the added concentrations of 1-[2-(decylthio)ethyl]azacyclopentane-2-one

| Concentrations (%) | Observation just after preparation | Observation after 3 days standing | Observation after 7 days standing |
| --- | --- | --- | --- |
| 10.0 | White emulsified | White emulsified | White emulsified |
| 5.0 | White emulsified | White emulsified | White emulsified |
| 2.0 | White clear | White clear | White clear |
| 1.0 | White clear | White clear | White clear |
| 0.5 | Colorless clear | Colorless clear | Colorless clear |
| 0.1 | Colorless clear | Colorless clear | Colorless clear |
| 0.01 | Colorless clear | Colorless clear | Colorless clear |
| 0 | Colorless clear | Colorless clear | Colorless clear |

Referential Experiment 3

Absorption Test on Rats (1) Preparation of composition for nasal administration containing PTH (a) Preparation A An emulsion for nasal administration containing PTH of the present invention was prepared in the followings.

A paraben solution 80 ml was prepared in advance by dissolving methyl p-oxybenzoate and propyl p-oxybenzoate in distilled water at 80° C.

2.2 g of glycerol and 1 g of dipotassium glycyrrhizate were added to the paraben solution and dissolved by agitation. 1 g of 1-[2-(decylthio)ethyl] azacyclopentan-2-one was added thereto. The solution was adjusted to pH 5.5 with 1N sodium hydroxide, and the volume was made up to 100 ml with the paraben solution. The mixture was emulsified by agitation using Biomixer (NIHON SEIKI SEISAKUSHO, Type ABM) at 15,000 rpm for 3 minutes to prepare the emulsion. 0.607 mg of h-PTH (1–34) (specific activity, 3,300 Units/mg*; teriparatide acetate, Toyo Jozo Co.) was dissolved in 10 ml of the emulsion hereinabove to prepare the composition hereinbelow.

In 1 ml of the emulsion for nasal administration;

| | | |
| --- | --- | --- |
| ① h-PTH(1-34) | 200 | Units |
| ② 1-[2-(decylthio)ethyl] azacyclopentan-2-one | 10 | mg |
| ③ dipotassium glycyrrhizate | 10 | mg |
| ④ glycerol | 22 | mg |
| ⑤ methyl p-oxybenzoate | 1.2 | mg |
| ⑥ propyl p-oxybenzoate | 0.3 | mg |
| ⑦ sodium hydroxide appropriate volume, adjusted to pH 5.5 | | |
| ⑧ distilled water for injection total volume make up to 1 ml | | |

(i) Preparation of PTH receptor:

Male.SD rats, (body weight 200–250g) were decapitated, bled and laparotomized, thereafter the kidneys were extracted. Surface membrane of the kidney was removed off, then cortex was cut off and ice-cooled. All the operation of the following procedure was conducted as lower temperature (0°–4° C.) as possible. The cortex of the kidney was immersed in 10 mM Tris-HCl buffer solution (pH 7.5) containing 0.25M sucrose and 1 mM EDTA (hereinafter designates as buffer solution-A), and homogenized by glass-homogenizer using Teflon-pestle with adding three times amount (ml) of the buffer solution-A as much as of wet weight (g) of the kidney. The homogenate was centrifuged at 150×G for 10 minutes, and the supernatant was further centrifuged at 2200×G for 15 minutes. The supernatant liquid was discarded and the upperlayer milky emulsion in precipitate was suspended in the buffersolution-A, then the suspension was washed by centrifugation at 25000×G for 15 minutes. Resuspended emulsion was divided into vessels, freeze dried at −70° C. and stored at −20° C.

(ii) Reaction with PTH and PTH receptor:

Test samples were dissolved in 100 mM Tris-HCl buffer solution (pH 7.5) containing ATP-Mg 2 mM, $MgCl_2$ 10 mM, KCl 60 mM, GTP 20 μm, isobutyl methylxanthine 1 mM, creatine phosphate 8 mM and bovine serum albumin (BSA) 0.2% (hereinafter designates as buffer solution-B) so as to prepare concentration at 2 μg/ml and 10 μg/mi. The same preparation was made with dissolving standard sample of teriparatide acetate*.

The above prepared each solution (50 μl) of four types was divided separately into eight test tubes. All the test samples were kept in ice-cooled water in order to prevent decomposition of ATP and other components. PTH-receptor preparation hereinabove prepared, which was stored at −20° C., was defrosted at room temperature, and erealine kinase dissolved in buffer solution-A was added therein, so as to prepare concentration of creatine kinase 0.1 mg/ml and PTH receptor preparation 1.4 mg protein/ml, then the solutions were kept in ice.

The test sample solutions of the above four types were placed in warm-bath at 37° C., and the above PTH receptor-creatine kinase solution, each 50 μl, was added thereto, then incubated at 37° C. for 10 minutes. 0.1M acetate buffer solution (pH 4.0) 100 μl was added into each test tube, which was immediately put into ice-cooled water, thereafter all the test tubes were heatd in boiling water in order to stop the reaction.

(iii) Assaying the generated c-ATP:

The above heat-treated test samples were diluted with distilled water up to 10–30 times of volume and centrifuged at 2000×G for 15 minutes for deproteinization. c-ATP in the supernatant solution was assayed by RIA kit (YAMASA SHOYU CO.).

(iv) Assaying PTH activity:

An amount of assayed c-ATP is expressed by p mol/mg (PTH receptor protein)/min. which is set to the volume resulted by the reaction. Assayed value of PTH in the test sample in comparison with that of the standard sample of teriparatide hydrochloride is tested by the parallel line (2×2 points) test.

* Activity of teriparatide acetate is expressed by a teriparatide acetate unit according to a bioassay method using cell membrane of rat kidney cortex with a standard sample of teriparatide acetate.

Teriparatide acetate unit is defined by relative activity of standard sample of teriparatide acetate in comparison with a standard sample of bovine PTH(1-84) measured by the assay method hereinabove described and is determined as 3300 Units/mg.

(b) Control preparation B:

An emulsion for nasal administration containing PTH without 1-[2-(decylthio)ethyl]azacyclopentane-2-one, a control preparation, was prepared as follows for comparison with the present invention.

A paraben solution 80 ml was prepared in advance by dissolving in distilled water at 80° C. Glycerol 2.2 g and dipotassium glycyrrhizate 1 g were added to the paraben solution and dissolved by agitation. The solution was adjusted to pH5.5 with 1N sodium hydroxide, and the volume was made up to 100 ml with the paraben solution.

The h-PTH (1–34) (relative activity 3300 Units/mg) 0.607 mg was dissolved in the emulsion 10 ml hereinabove to prepare the composition hereinbelow. In 1 ml of the emulsion for nasal administration:

| | | |
|---|---|---|
| ① h-PTH(1-34) | 200 | Units |
| ② dipotassium glycyrrhizate | 10 | mg |
| ③ glycerol | 22 | mg |
| ④ methyl p-oxybenzoate | 1.2 | mg |
| ⑤ propyl p-oxybenzoate | 0.3 | mg |
| ⑥ sodium hydroxide appropriate volume, adjusted to pH 5.5 | | |
| ⑦ distilled water for injection total volume make up to 1 ml | | |

(2) Nasal administration test of h-PTH(1–34) preparation on rats:

Male, wister rats, (body weight 200–250 g) 3 rats in a group, fasted for 17 hours, were used for experiment. At 20 minutes before administration, rats were anesthetized with pentobarbital (50 mg/kg) by intraperitoneal injection. A cervical region of the rat was incized and polyethylene tube was inserted into the trachea according to a method by Hirai et al. [Int. J. Pharm., 9, 165 (1981)], then the incized part was closed by bonding with adhesives. Immediately after administration of h-PTH (1–34) 20 Units/0.1 ml/kg into external nares using microsyringe, the external naris was closed by adhesives.

Each 0.25 ml of the blood was collected from femoral vein 5 minutes before administration, at intervals of 5, 10, 20, 30, 45 minutes, and 1, 1.5 and 2 hours after administration. Collected blood samples were centrifuged at 15000 rpm for 5 minutes and the separated plasma was kept freezing at −30° C. until used for the assay. h-PTH(1–34) plasma level were evaluated by a RIA with two antibodies using INS-PTH kit(NICOLS CORP.).

(3) Result:

Blood levels of h-PTH(1–34) after nasal administration (20 Units/kg) of the above preparation A and the control preparation B are shown in FIG. 1. For comparison, blood level of h-PTH (1–34) after intramusclar injection (10 Units/kg) is shown. Preparation which contains 1% of 1-[2-(decylthio) ethyl]-azacyclopentane-2-one of the present invention exhibited much satisfactory absorption, and the emulsion preparation of the present invention has shown significantly superior absorption activity of h-PTH when compared with the control preparation B.

Also an absorption ratio of the emulsion preparation of the present invention on rat has shown the value of 37% as compared with that of administration of intramuscular injection on the area under the blood concentration-time curve (AUC).

Accordingly, it is obvious that the emulsion preparation of the present invention has significantly improved the nasalh-PTH (1–34) absorbability when compared with the control preparation B, and are proved to be a useful preparation in place of intramuscular administration, due to the superior biological availability.

In Fig. 1, — — shows the results of intramuscular administraion of h-PTH(1–34)(10 Units/kg) as the control; — — shows the results of nasal administration of preparation A obtained in (a) of the referential experiment 3; and — — shows the results of nasal administration of the control preparation B obtained in (b) of the referential experiment 3.

Preferable examples of the PTH emulsion for nasal administration of the present invention will be described hereinbelow,

Example 1

Emulsions for nasal administration were prepared using the following amounts (per 1 ml) of ingredients:

| | | |
|---|---|---|
| ① h-PTH(1-34) | 200 | Units |
| ② 1-[2-(decylthio)ethyl] azacyclopentan-2-one | 5 | mg |
| ③ dipotassium glycyrrhizate | 10 | mg |
| ④ glycerol | 22 | mg |
| ⑤ methyl p-oxybenzoate | 1.2 | mg |
| ⑥ propyl p-oxybenzoate | 0.3 | mg |
| ⑦ sodium hydroxide appropriate volume, adjusted to pH 5.5 | | |
| ⑧ distilled water for injection total volume make up to 1 ml | | |

The resulting emulsions were aseptically filtered through a membrane filter of 0.22 μm, and aseptically filled in vials for nasal administration, to obtain the final preparation.

Example 2

Emulsions for nasal administration were prepared using the following amounts (per 1 ml) of ingredients:

| | | |
|---|---|---|
| ① h-PTH(1-34) | 200 | Units |
| ② 1-[2-(decylthio)ethyl] azacyclopentan-2-one | 10 | mg |
| ③ dipotassium glycyrrhizate | 10 | mg |
| ④ glycerol | 22 | mg |
| ⑤ methyl p-oxybenzoate | 1.0 | mg |
| ⑥ sodium hydroxide appropriate volume, adjusted to pH 5.5 | | |
| ⑦ distilled water for injection total volume make up to 1 ml | | |

The resulting emulsions were aseptically filtered through a membrane filter of 0.22 μm, and aseptically filled in vials for nasal administration, to obtain the final preparation.

Example 3

Emulsions for nasal administration were prepared using the following amounts (per 1 ml) of ingredients:

| | | |
|---|---|---|
| ① h-PTH(1-34) | 100 | Units |
| ② 1-[2-(decylthio)ethyl] azacyclopentan-2-one | 10 | mg |
| ③ dipotassium glycyrrhizate | 10 | mg |
| ④ glycerol | 21 | mg |
| ⑤ methyl p-oxybenzoate | 1.2 | mg |
| ⑥ propyl p-oxybenzoate | 0.3 | mg |
| ⑦ sodium hydroxide appropriate volume, adjusted to pH 5.5 | | |
| ⑧ distilled water for injection total volume make up to 1 ml | | |

The resulting emulsions were aseptically filtered through a membrane filter of 0.22 μm, and aseptically filled in vials for nasal administration, to obtain the final preparation.

EFFECT OF THE INVENTION

In the present invention, homogeneous and stable emulsions for nasal administration containing PTH are available by using an azacycloalkane derivative as the absorption promotor and glycyrrhizic acid or its non-toxic salt. The obtained emulsions exhibit satisfactory bio-availability with superior absorbability through nasal mucosa and less adverse effedct to nasal mucosa, as compared to the conventional nasal administration preparations. Thus, the practical use of the PTH emulsions for nasal administration is enabled by the present invention.

We claim:

1. A parathyroid hormone-containing emulsion for nasal administration, comprising parathyroid hormone as the active ingredient, and containing, at least, an azacycloalkane derivative of the formula [1]:

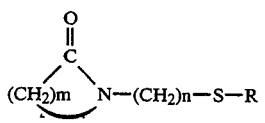

wherein R is alkyl, m is an integer of 2-4, and n is an integer of 1-15, provided that R is alkyl of $C_{5-11}$ in case where n is 1-3, as the absorption promotor, glycyrrhizic acid or its non-toxic salt, and a suitable amount of water.

2. An emulsions according to claim 1 wherein the azacycloalkane derivative of the formula [1] is 1-[2-(decyl thio)ethyl ]azacyclopentan-2-one, wherein R is alkyl of $C_{10}$, m is 3, and n is 2.

3. An emulsions according to claim 1 wherein the content of parathyroid hormone is 10–10,000 Units per 1 ml of the emulsion.

4. An emulsions according to claim 1 wherein the amount of glycyrrhizic acid or its non-toxic salt is 0.1–5% (W/V) per emulsion.

5. An emulsions according to claim 1 wherein the amount of azacycloalkane derivative is 0.1–10% (W/V) per emulsion.

6. An emulsions according to claim 1 comprising human parathyroid hormone (1–34), glycyrrhizic acid or its non-toxic salt and 1-[2-(decyl thio)ethyl]-azacyclopentan-2-one.

7. An emulsion according to claim 4 wherein the non-toxic salt of glycyrrhizic acid is dipotassium glycyrrhizate.

8. An emulsion according to claim 1 wherein the pH of emulsion is ph 5–7.

9. An emulsion according to claim 1 wherein the emulsion is an oil in water type emulsion with 0.1–0.3 μm particle size.

* * * * *